United States Patent
Lorenz et al.

(10) Patent No.: US 9,267,874 B2
(45) Date of Patent: Feb. 23, 2016

(54) METHOD AND SYSTEM FOR DETECTING CORROSION OF AN INSULATED CORROSION PRONE OBJECT

(75) Inventors: Maarten Lorenz, Amsterdam (NL); Gerald Sprachmann, Amsterdam (NL)

(73) Assignee: Shell Oil Company, Houston, TX (US)

( * ) Notice: Subject to any disclaimer, the term of this patent is extended or adjusted under 35 U.S.C. 154(b) by 69 days.

(21) Appl. No.: 13/884,232

(22) PCT Filed: Nov. 9, 2011

(86) PCT No.: PCT/EP2011/069718
§ 371 (c)(1),
(2), (4) Date: May 8, 2013

(87) PCT Pub. No.: WO2012/062792
PCT Pub. Date: May 18, 2012

(65) Prior Publication Data
US 2013/0224867 A1 Aug. 29, 2013

(30) Foreign Application Priority Data
Nov. 9, 2010 (EP) .................................. 10190469

(51) Int. Cl.
*G01N 17/00* (2006.01)
(52) U.S. Cl.
CPC .................................... *G01N 17/00* (2013.01)
(58) Field of Classification Search
CPC .................................................... G01N 17/00
USPC ............................................ 422/53; 436/2, 6
See application file for complete search history.

(56) References Cited

U.S. PATENT DOCUMENTS

| | | | | |
|---|---|---|---|---|
| 3,642,308 A | * | 2/1972 | Zeile et al. | 285/47 |
| 3,665,968 A | * | 5/1972 | De Putter | 138/141 |
| 4,013,924 A | * | 3/1977 | Christensen et al. | 361/49 |
| 4,189,938 A | * | 2/1980 | Heim | 73/40.7 |
| 4,271,120 A | * | 6/1981 | Michaud | 422/53 |
| 4,779,453 A | * | 10/1988 | Hopenfeld | 73/86 |
| 5,036,287 A | * | 7/1991 | Serwatzky | 324/700 |
| 5,526,689 A | | 6/1996 | Coulter et al. | 73/592 |
| 6,171,025 B1 | * | 1/2001 | Langner et al. | 405/154.1 |
| 8,001,990 B2 | * | 8/2011 | Schmidt | 137/78.3 |
| 8,810,264 B2 | * | 8/2014 | Bohon et al. | 324/700 |
| 2010/0319435 A1 | * | 12/2010 | Strong | 73/25.04 |
| 2012/0056634 A1 | * | 3/2012 | Bohon et al. | 324/700 |

FOREIGN PATENT DOCUMENTS

| | | | |
|---|---|---|---|
| GB | 2368914 | 5/2002 | ............. G01N 17/00 |
| KR | 20060015152 | 2/2006 | ............. G01N 17/00 |
| WO | WO0045148 | 8/2000 | ............. G01N 17/02 |
| WO | WO2009126802 | 10/2009 | ............. C09D 5/08 |

OTHER PUBLICATIONS

PCT International Search Report, Application No. PCT/EP2011/069718 dated Jan. 24, 2012.

* cited by examiner

*Primary Examiner* — Arlen Soderquist

(57) ABSTRACT

Corrosion Under Insulation (CUI) of an insulated iron or other corrosion prone object (1) is detected by taking a sample (8) of the pore fluid from the pores of a permeable insulation layer (2) that covers at least part of the object (1) and analyzing the composition of the sample (8) on the presence of any tracer fluid, such as phospines, mercaptans, alcohols, acids, ketones and/or aldehydes emitted or acetic acid and/or butoxyethanol absorbed by any corrosion of the corrosion prone object (1) by a tracer fluid detection sensor (6).

15 Claims, 2 Drawing Sheets

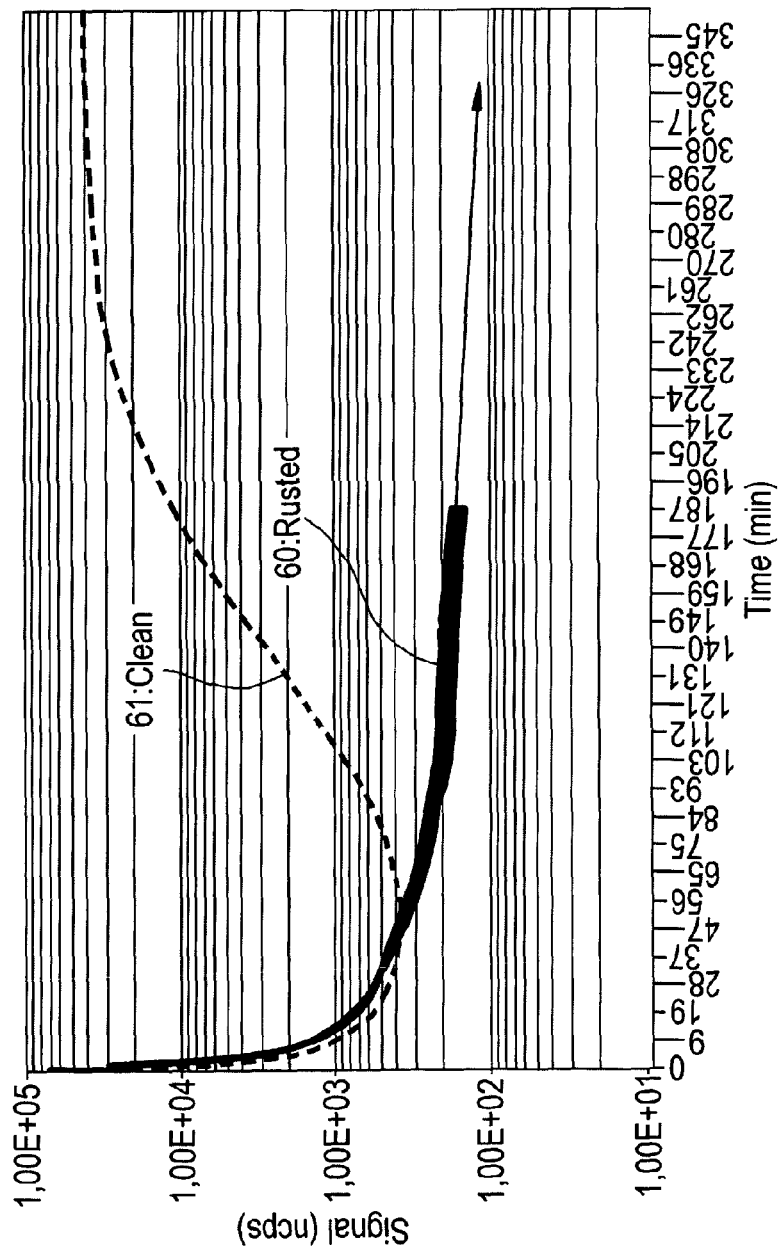

METHOD AND SYSTEM FOR DETECTING CORROSION OF AN INSULATED CORROSION PRONE OBJECT

PRIORITY CLAIM

The present application claims priority from PCT/EP2011/069718, filed Nov. 9, 2011, which claims priority from European application 10190469.6, filed Nov. 9, 2010, which is incorporated herein by reference.

BACKGROUND OF THE INVENTION

The invention relates to a method and system for detecting corrosion of an insulated corrosion prone object.

Inspection of insulated corrosion prone objects generally requires removal of at least part of the insulation layer to facilitate the inspection and subsequent reinstallation of the insulation layer.

International patent application WO 00/45148 discloses the use of corrosion sensors contained within the thermally insulating layer of a metal pipe, wherein the corrosion sensors comprise an electrochemical corrosion cell, an electrochemical noise measuring apparatus and/or an electrode assembly to indicate the presence of an electrolyte in the insulation layer, so that the known method uses the presence of an electrically conductive electrolyte as a tracer for the presence of corrosion of the metal pipe.

Japanese patent applications JP63079053 and JP58167948 disclose electrochemical and electrode assemblies for measuring corrosion of metal objects.

International patent application WO2008/047068 discloses a method for detecting moisture in an insulation layer surrounding an insulated vessel or pipe, wherein radially separated fiber optical Distributed Temperature Sensor (DTS) assemblies are configured to determine any differential temperature across the monitored section of insulation, which differential temperature is used as an indication of the possible presence of moisture in the insulation layer.

The paper "The two odors of iron when touched or pickled: (Skin) Carbonyl compounds and organophospines" published by D. Glindemann, A. Dietrich, H. J. Staerk and P. Kuschk in the magazine Angewandte Chemie, Edition 2006, 45, 7006-7009 discloses that phosphorus- and carbon-rich cast iron and steel under attack by acid emit a garlic-carbide metallic odor, which is dominated by volatile organophosphines and phosphine ($PH_3$).

Other known methods for inspecting corrosion prone objects on the presence of corrosion are disclosed in UK patent application GB 2368914, Kroatian patent KR20060015152 and International patent application WO2009/126802.

There is a need for an improved method for inspecting insulated corrosion prone objects on Corrosion Under Insulation (CUI) in a substantially non intrusive manner, which does not require the use of complex electrode assemblies and which does not damage and/or require removal and reinstallation of the insulation layer.

SUMMARY OF THE INVENTION

In accordance with the invention there is provided a method for detecting corrosion of an insulated corrosion prone object, which is at least partly covered by a permeable insulation layer with pores containing a pore fluid, the method comprising taking a sample of the pore fluid and analyzing the composition of the sample for the presence of any tracer fluid emitted or absorbed by any corrosion of the corrosion prone object, wherein the sample is taken by injecting a sweep fluid into the pores of the permeable insulation layer and capturing a mixture of the sweep fluid and the core fluid and any tracer fluid from the permeable insulation layer.

If the insulation layer has a low permeability then the sample may be taken by stabbing a hollow needle into the insulation layer and excavating through the needle an amount of pore fluid for analysis.

If the corrosion prone object comprises rust prone iron, such as carbon steel, then the tracer fluid may comprise phosphine, mercaptans, alcohols, acids, ketones, aldehydes, and/or any other chemical composition released during iron oxidation.

The phosphine gas may comprise phosphine ($PH_3$) and/or organophosphine. The organophosphine may comprise $CH_5PO_2$, known as Methyl Phosphinic Acid or MPA. The mercaptans may comprise methylmercaptan ($CH_4S$), the alcohols methanol ($CH_4O$), the acids acetic acid ($C_2H_4O$), the ketons acetone ($C_3H_6O$) and the aldehydes acetaldehyde ($C_2H_5O$).

The permeable insulation layer may be arranged between an outer surface of the corrosion prone object and an inner surface of a substantially impermeable protective layer, in which case the sweep fluid may be injected through a tracer fluid injection conduit, which is stabbed through the protective layer into the permeable insulation layer. In such case the mixture of the sweep fluid, the core fluid and any tracer fluid may be captured through a fluid excavation conduit, which is stabbed through the protective layer into the permeable insulation layer.

Optionally, the fluid excavation conduit co-axially surrounds the sweep fluid injection conduit.

If the corrosion prone object is an insulated tubular, which is surrounded by tubular permeable insulation and protective layers then the sweep fluid injection conduit may be stabbed near one end of the insulated tubular through the wall of the impermeable layer into pores of the permeable insulation layer and the fluid excavation conduit may be stabbed near another end of the insulated tubular through the wall of the impermeable layer into pores of the permeable layer. The insulated tubular may be a carbon steel oilfield tubular or a carbon steel tubular or vessel in a crude oil and/or gas natural gas processing or oil refinery plant and the method is used for non-intrusive inspection of the tubular on the presence of rust, and the tubular is approved for processing of hydrocarbon fluid if the fluid mixture comprising sweep fluid, pore fluid and any tracer fluid comprises up to a predetermined maximum content of phosphine gas, mercaptans, alcohols, acids, ketones, aldehydes, and/or any other chemical composition released during iron oxidation.

The sweep fluid may comprise a reactive rust tracer component which reacts with rust and/or other corrosion products. If the corrosion prone object comprises iron then the reactive rust tracer component may comprise acetic acid and/or butoxyethanol, which reacts with and is therefore absorbed by rust.

The sweep fluid may comprise a non-reactive component, such as air, an inert gas, such as nitrogen and/or a mix of air/inert gas and the reactive rust tracer component, such as acetic acid, phosphoric acid and/or butoxyethanol, which reactive rust tracer component reacts with rust and/or other corrosion products to provide a quantitative evaluation of the size of a corroded area of the corrosion prone object. The reactive rust tracer component may be added in a small amount to the sweep fluid.

In accordance with the invention there is further provided a system for detecting corrosion of a surface of a corrosion prone object which is at least partly covered by a permeable insulation layer that comprises pores with a pore fluid, wherein the permeable insulation layer is arranged between an outer surface of the corrosion prone object and an inner surface of a protective layer, the system comprising a fluid excavation conduit for capturing a sample of the pore fluid from the permeable insulation layer, which sample can be taken by injecting a sweep fluid through a tracer fluid injection conduit into the pores of the permeable insulation layer, and means analyzing the composition of the sample on the presence of any tracer fluid emitted or absorbed by any corrosion of the corrosion prone object.

These and other features, embodiments and advantages of the method and/or system according to the invention are described in the accompanying claims, abstract and the following detailed description of non-limiting embodiments depicted in the accompanying drawing, in which description reference numerals are used which refer to corresponding reference numerals that are depicted in the drawings.

BRIEF DESCRIPTION OF THE DRAWINGS

FIG. 2 is a graph showing results of an comparative experiment wherein acetic acid is injected into annuli surrounding clean and rusted steel cylinders, wherein in the latter case at least some of the injected acetic acid reacts with and is absorbed by the rust.

DETAILED DESCRIPTION OF THE DEPICTED EMBODIMENTS

Figure 1:
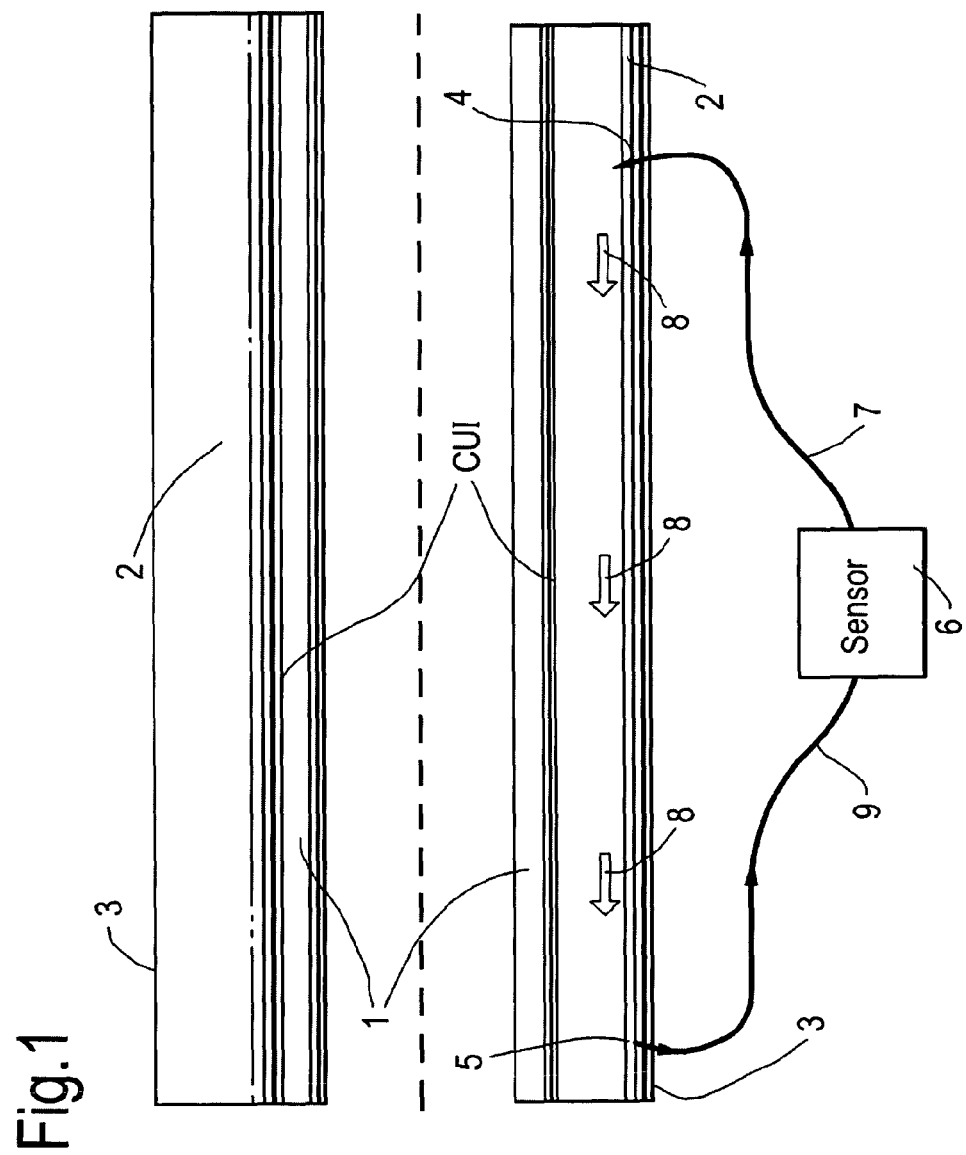
FIG. 1 depicts an insulated corrosion prone tubular, which is inspected on corrosion utilizing the method according to the invention.

FIG. 1 depicts a corrosion prone tubular object 1 of which the outer surface is covered by a porous and permeable insulation layer 2 of which the outer surface may be coated with a protective layer or cladding 3.

The pores of the insulation layer 2 are filled with a pore fluid of which a sample is optionally taken by injecting, as illustrated by arrow 4, a sweep fluid, such as air and/or an inert gas, via a sweep fluid injection conduit 7, which is stabbed through the protective layer or cladding 3 into the insulation layer 2. Arrow 5 illustrates how a fluid excavation conduit 9 is stabbed through the protective layer 3 into the insulation layer at a selected distance from the fluid injection conduit 4.

A mixture 8 of sweep fluid, pore fluid and any tracer fluid generated by corrosion of the corrosion prone tubular object 1 is excavated from the pores of the insulation layer via the fluid injection and excavation conduits 7 and 9 and fed into a sensor 6 which measures the concentration of tracer fluid, if any, in the mixture 8 of sweep gas, core fluid and any tracer fluid passing through the fluid injection and excavation conduits 7 and 9.

Optionally the pore fluid mixture 8 of sweep gas, core fluid and any tracer fluid is recycled back via the fluid excavation conduit 7 into the insulation layer 2 as illustrated by the arrows 4, 5 and 8 in FIG. 1.

It will be understood that instead of injecting a sweep fluid through a first hose 7 and detecting the composition of any sweep fluid, pore fluid and tracer fluid by means of a second hose 9 which is stabbed into the permeable insulation layer 2 at a distance from the first hose 7 the method according to the invention may be carried out with a single hose 7 through which a batch of the sweep fluid is initially injected into the permeable insulation layer 2 and through which subsequently sweep fluid, pore fluid and any tracer fluid is sucked out of the insulation layer 2. In such case the fluid injection and evacuation may be performed by stabbing an injection needle into the insulation layer 2, through which the sweep fluid is initially injected and through which subsequently the mixture of sweep, pore and tracer fluids is evacuated from the insulation layer 2. The non-intrusive Corrosion Under Insulation (CUI) detection method according to the invention is particularly useful to inspect an insulated corrosion prone steel object 1 on the presence of rust.

Rusting steel has a particular odour believed to be due to the emission of an organophospine (MPA) or phospine gas that is a by-product of the rusting process due to the presence of carbon and phosphorous components in the steel. Furthermore, rusting steel produces a specific emission pattern of compounds like mercaptans, alcohols, acids, ketones, aldehydes. By the use of a chemical sensor 6 and a circulating sweep-gas stream 8 through the pores of the permeable insulation layer 2 the sensor 6 is able to detect the presence of CUI when developing on the insulated corrosion prone tubular object 1.

The method and system according to the present invention permit effective monitoring of long stretches of piping 1 and/or large areas of vessels for CUI without the need for installing expensive scaffolding and such that safety problems are avoided which relate to removing insulation from hot piping 1 or shutting down piping 1 section all together to allow for inspection.

Investigation has shown that:
Rusting steel has a particular odour due to the emission of an organophosphine gas (methylphosphinic acid, or MPA, $CH_5PO_2$) and/or Phosphine gas;
Rusting steel produces a specific emission pattern of mercaptans, alcohols, acids, ketones, aldehydes;
MPA has been detected in concentrations of up to 3 mg/g of steel; and
The MPA, Phosphine, mercaptans, alcohols, acids, ketones, aldehydes are by-products of the rusting process and are due to the presence of carbon and phosphorous components in the steel.

Early detection of MPA/Phosphine, mercaptans, alcohols, acids, ketones, aldehydes under the insulation 2 indicates the onset of CUI, originating from iron oxides forming at a breach in the protective coating, before failure occurs.

The method according to the invention may be used to detect CUI on newly coated items 1 by detecting MPA/Phosphine, mercaptans, alcohols, acids, ketones, aldehydes using a chemical sensor 6.

By pumping clean air or an inert gas via sweep fluid injection conduit 4 into the insulation layer 2 at one point and extracting a pore fluid mixture 8 of sweep fluid, pore fluid and/or any tracer fluid from another point via fluid excavation conduit 5, a circulation flow may be created which passes through a MPA, phosphine and or other tracer fluid detection sensor 6.

The sensitivity of the corrosion detection system according to the invention may be enhanced by maintaining the circulation flow illustrated by arrows 4,5 and 8 for a longer period of time.

The system according to the invention provides an easily, flexible and low-cost deployable non intrusive CUI detection system since the sensor 6, pump and hoses 7 can be applied virtually anywhere; connected through holes 4,5 in the cladding 3 (which may be equipped with water detectors when not inspecting).

Provides an early warning signal, leaving time to repair protective coating barrier; approximate location can be found by reducing the length/area between hose connections 4 and 5, where the hoses 7 penetrate the cladding 3.

A highly sensitive multi component sensor 6 for detecting trace gases, such as MPA/Phosphine, mercaptans, alcohols, acids, ketones and/or aldehydes in the sampled pore fluid mixture 8 is commercially available and works best at higher temperatures and atmospheric pressure (most susceptible CUI range: 50-110° C., 1 bar).

This sensor 6 is a Proton Transfer Reaction-Mass Spectrometer, abbreviated as PTR-MS, marketed by the company Ionimed in Innsbruck, Austria.

The PTR-MS sensor 6 allows online measurements of trace components with concentrations as low as pptv in the sampled pore fluid mixture 8 up to a time response of 0.1 sec.

The ionization agent in the PTR-MS sensor 6 comprises $H_3O^+$ ions, and the buffer gas in which the ions are allowed to drift is the gas containing the trace compounds to be analyzed. $H_3O^+$ ions do not react with any compounds which have a proton affinity lower than $H_2O$, being 7.22 eV, but they do transfer their proton to VOC's, all of which—with the exception of a very few—have proton affinities larger than 7.22 eV.

Detection of organic reactants [R] having low volume mixing ratios (VMR's) in the fluid mixture 8 rely on exothermic proton transfer reactions:

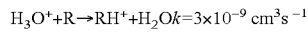

At the end of the reaction section the density of product ions $[RH^+]$ in the fluid mixture 8 detected by the PTR-MS sensor 6 is given by:

$$[RH^+]=[H_3O^+]_0(1-e^{-k[R]t})\approx[H_3O^+]_0[R]\,kt$$

The method according to the invention may be used to detect Corrosion Under Insulation (CUI) on external surfaces of insulated pipes 1 and/or other equipment surface, and also at complex structures, like iron reinforcement rods of concrete structures, supports or other insulated metal or other corrosion prone objects. As an alternative to detecting substances that are being released when steel corrodes, the uptake of a rust reactive sweep fluid by steel corrosion products, such as rust, may be detected in accordance with the method according to the invention.

The uptake may be detected by injecting a sweep fluid mixture that comprises, in substantially equal volumes, both the rust reactive sweep fluid (for example acetic acid: $CH_3COOH$, and/or butoxyethanol) and another, inert or non-reactive, sweep fluid (for example $N_2$ and/or MeOH), which will not react with anything, into the space 2 between the cladding 3 and the corrosion prone surface 1. When extracting the sweep and pore fluid mixture from the insulation layer 2, a difference in concentration between the rust reactive sweep fluid ($CH_3COOH$) and the inert sweep fluid (for example $N_2$ and/or MeOH) will provide an indication of the size of the corroded area.

For corrosion prone steel objects the rust reactive sweep fluid may comprise acetic acid ($CH_3COOH$) that adheres to the corrosion products ($Fe_2O_3$ and/or $FeO(OH)$) on the basis of the following chemical reactions:

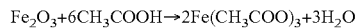

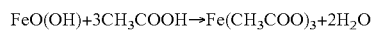

FIG. 2 shows the results of a laboratory test wherein acetic acid ($CH_3COOH$) is injected into an annular space 2 surrounding a clean steel cylinder 1 and an annular space surrounding a rusted steel cylinder 1 of a similar size as the clean, unrusted steel cylinder 1.

Line 60 shows the amount of acetic acid returned from the annulus surrounding the rusted steel cylinder 1 and line 61 shows the amount of acetic acid returned from the annulus surrounding the clean, unrusted, steel cylinder 1.

Lines 60 and 61 show that the amount of acetic acid returned from the annulus surrounding the clean, unrusted, cylinder 1 is larger than the amount of acetic acid returned from the annulus surrounding the annulus surrounding the rusted cylinder 1. The difference is expected to result from the chemical reactions between rust and acetic acid shown above.

The experiment shows that there is a distinct relation between the presence of steel corrosion products and the concentration of returned acetic acid.

There may be other reactive rust tracers that act similar as acetic acid, such as butoxyethanol. The advantages of the reactive tracer fluid absorption method illustrated in FIG. 2 are that:

The corrosion does not have to be active (no moisture needs to be present);

If corrosion products are detected in the first measurements and none are detected in following measurements after certain periods of time, it may be concluded that the corrosion is not active anymore and, as such, may not be a threat anymore; this is possible because the reaction of the special substance with the corrosion products present is irreversable, i.e. the corrosion products cannot be detected once again in a next measurement; and The concentration drop of the reactive substance, such as acetic acid or butoxyethanol, seems to be (linearly) related to the corroded area, which allows for classification based on the extent of the corrosion under insulation (CUI).

What is claimed is:

1. A method for detecting corrosion of an insulated corrosion prone object, which is at least partly covered by a permeable insulation layer with pores containing a pore fluid, wherein the permeable insulation layer is arranged between an outer surface of the corrosion prone object and an inner surface of a protective layer, the method comprising taking a sample of the pore fluid and analyzing the composition of the sample for the presence of any tracer fluid emitted or absorbed by any corrosion of the corrosion prone object, wherein the sample is taken by injecting a sweep fluid through a tracer fluid injection conduit into the pores of the permeable insulation layer and capturing a mixture of the sweep fluid and the pore fluid and any tracer fluid from a fluid excavation conduit through the permeable insulation layer.

2. The method of claim 1, wherein the corrosion prone object comprises rust prone iron, such as carbon steel.

3. The method of claim 2, wherein the tracer fluid comprises phosphines, mercaptans, alcohols, acids, ketones, aldehydes and/or any other chemical composition released during iron oxidation.

4. The method of claim 3, wherein the tracer fluid comprises phosphine ($PH_3$), organophosphine, methylmercaptan ($CH_4S$), methanol ($CH_4O$), acetic acid ($C_2H_4O$), acetone ($C_3H_6O$) and/or acetaldehyde ($C_2H_5O$).

5. The method of claim 4, wherein the tracer fluid comprises organophosphine comprising $CH_5PO_2$, known as Methyl Phosphinic Acid or MPA.

6. The method of claim 1, wherein the sweep fluid comprises a reactive rust tracer which reacts with and is therefore absorbed by rust and/or other corrosion products.

7. The method of claim 6, wherein the sweep fluid comprises air, an inert gas and the reactive rust tracer, which comprises acetic acid, phosphoric acid, butoxyethanol, and/or any other reactive rust tracer compound that reacts with rust and/or other corrosion products to provide a quantitative evaluation of the size of a corroded area of the corrosion prone object.

8. The method of claim 1, wherein the protective layer is substantially impermeable.

9. The method of claim 8, wherein the tracer fluid injection conduit is stabbed through the protective layer into the permeable insulation layer.

10. The method of claim 9, wherein the fluid excavation conduit is stabbed through the protective layer into the permeable insulation layer.

11. The method of claim 1, wherein the fluid excavation conduit co-axially surrounds the tracer fluid injection conduit.

12. The method of claim 1, wherein the corrosion prone object is an insulated tubular, which is surrounded by tubular insulation and protective layers and the tracer fluid injection conduit is stabbed near one end of the insulated tubular through the wall of the protective layer into pores of the permeable insulation layer and the fluid excavation conduit is stabbed near another end of the insulated tubular through the wall of the protective layer into the pores of the insulation layer.

13. The method of claim 12, wherein the insulated tubular is a carbon steel oilfield tubular or a carbon steel tubular or vessel in a crude oil and/or gas natural gas processing or oil refinery plant and the method is used for non-intrusive inspection of the tubular on the presence of rust, and the tubular is approved for processing of hydrocarbon fluid if the fluid mixture comprising sweep fluid, pore fluid and any tracer fluid comprises up to a predetermined maximum content of phosphine, mercaptans, alcohols, acids, ketones, aldehydes and/or any other chemical composition released during iron oxidation.

14. The method of claim 13, wherein the fluid excavation conduit comprises a sensor which determines the content of phosphine, MPA, mercaptans, alcohols, acids, ketones, aldehydes and/or another tracer fluid in the fluid mixture.

15. A system for detecting corrosion of a surface of a corrosion prone object, which is at least partly covered by a permeable insulation layer that comprises pores with a pore fluid, the system comprising a protective layer surrounding the corrosion prone object, the permeable insulation layer being arranged between an outer surface of the corrosion prone object and an inner surface of the protective layer, the system further comprising a fluid excavation conduit for capturing a sample of the pore fluid from the permeable insulation layer, a tracer fluid injection conduit for injecting a sweep fluid into the pores of the permeable insulation layer, and means for analyzing the composition of the sample for the presence of any tracer fluid emitted or absorbed by any corrosion of the corrosion prone object.

* * * * *